(12) United States Patent
Juto

(10) Patent No.: US 6,193,707 B1
(45) Date of Patent: *Feb. 27, 2001

(54) METHOD, DEVICE AND SYSTEM FOR POSITIONING A PROBE ON A TARGET SURFACE IN AN OPEN CAVITY IN A TEST OBJECT

(76) Inventor: Jan-Erik Juto, Linnégatan 86, 115 23 Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,252
(22) PCT Filed: May 17, 1996
(86) PCT No.: PCT/SE96/00648
　§ 371 Date: Nov. 6, 1997
　§ 102(e) Date: Nov. 6, 1997
(87) PCT Pub. No.: WO96/36270
　PCT Pub. Date: Nov. 21, 1996

(30) Foreign Application Priority Data

May 18, 1995 (SE) .................................................... 9501842

(51) Int. Cl.⁷ ................................................. A61B 17/00
(52) U.S. Cl. ............................................. 606/1; 606/130
(58) Field of Search .................. 606/130, 1; 600/417, 600/429; 128/898

(56) References Cited

U.S. PATENT DOCUMENTS

| | | |
|---|---|---|
| 5,184,601 | 2/1993 | Putman . |
| 5,228,429 | 7/1993 | Hatano . |
| 5,591,175 * | 1/1997 | Juto ...................................... 606/130 |
| 5,666,957 * | 9/1997 | Juto ...................................... 606/130 |
| 5,695,501 * | 12/1997 | Carol et al. ........................... 606/130 |

FOREIGN PATENT DOCUMENTS

| | | |
|---|---|---|
| 1907235 | 8/1970 | (DE) . |
| 4116810 A1 | 11/1992 | (DE) . |
| 0412282 A1 | 2/1991 | (EP) . |

OTHER PUBLICATIONS

"Rhinostereometry", Jan–Erik Juto, Department of otorhinolaryngology, Södersjukhuset, Stockholm, 1985.

* cited by examiner

*Primary Examiner*—Glenn K. Dawson
(74) *Attorney, Agent, or Firm*—Burns, Doane, Swecker & Mathis, LLP

(57) ABSTRACT

In a method for positioning the end (63) of a probe (60) on a target surface inside an open cavity in a test object, preferably on the nasal mucous membrane of a human being, the test object is fixed in a given position, whereupon an optical instrument (1) is so adjusted that the target surface is located essentially on its optical axis (I) and the position of the target surface in the longitudinal direction of the optical axis is defined. Then, the probe is attached on a holder (2), which is so operated that the end of the probe is placed essentially on the optical axis and is moved along this axis to the target-surface position defined with the aid of the optical instrument. A device and a system for implementing this method are also disclosed.

13 Claims, 2 Drawing Sheets

METHOD, DEVICE AND SYSTEM FOR POSITIONING A PROBE ON A TARGET SURFACE IN AN OPEN CAVITY IN A TEST OBJECT

FIELD OF THE INVENTION

This invention relates to a method, a device and a system for positioning a probe on a target surface in an open cavity in a test object. The open cavity may, for instance, be a body cavity of a human being or an animal, especially the nasal cavity.

BACKGROUND OF THE INVENTION

Occupying an exposed and fairly immovable position directly on the bone, the nasal mucous membrane is a suitable object of study. When studying the nasal mucous membrane, one occasionally wishes to insert a probe to a carefully determined position in the nose, for instance in order to introduce a chemical substance whose effect on the mucous membrane is to be studied, or in order to carry out a measurement directly on the mucous membrane, for instance measure the circulation in the mucous membrane with the aid of a Doppler laser. In this measurement, the probe has to be placed in a highly exact position in relation to the mucous membrane. The probe must not, for example, press against the mucous membrane, since the pressure might then trigger defence mechanisms altering the circulation. As a result, positioning accuracy in the order of a tenth of a millimeter or so is required. Owing to tremblings of the hand, hair blocking the view and the darkness in the nasal cavity, it is, of course, extremely difficult to manually position a probe so exactly on the nasal mucous membrane. Consequently, previous measurements have not yielded as reliable results as would be desired.

SUMMARY OF THE INVENTION

One object of the invention is, therefore, to provide a method, a device and a system enabling highly exact positioning of an end of a probe on a given location in the nasal cavity.

According to the invention, this object is achieved by a method, a device and a system having the characteristics recited in appended claims 1, 6 and 12, respectively. Preferred embodiments are defined in the sub-claims.

To be more specific, it has been found that one may perform highly exact positioning, which in addition can be repeated with a high degree of repeatability, by using a combination of optical technique for defining the place on the mucous membrane where one wishes to position the probe and a device of special design for bringing the probe to this place.

A suitable prior-art optical technique that may be used for implementing the invention is rhinostereometry, which is described in a doctoral thesis written by Jan-Erik Juto and entitled "Rhinostereometry", the Department of Otorhinolaryngology, Södersjukhuset, Stockholm, 1985, Sweden. A rhinostereometer consists of a microscope which is mounted on a micrometer table. The lens and the eyepiece of the microscope are so chosen as to result in a very shallow depth of field. Today, the rhinostereometer is used for measuring the swelling of the nasal mucous membrane, in which case a small piece of the mucous membrane is observed through the microscope and the swelling is measured with the aid of a scale in the eyepiece.

Thus, the rhinostereometer is located outside the cavity to be examined, which is an advantage, it being as problematic to position an optical instrument introduced into the nose as to position a probe. In addition, there is not much place for the insertion of an optical instrument, the discomfort experienced by the patient is accentuated, and there is a risk of hitting the mucous membrane so that this is interfered with, resulting in less exact later measurements.

However, one problem associated with the use of the above optical technique for introducing a probe into the nose is that the space between the lens of the microscope and the nose is restricted, it being necessary to place the lens close to the nose in order to obtain satisfactory light conditions. On the other hand, a probe that is to be inserted in the nose must have an essentially rectilinear and rigid end portion having a length of about 4–5 cm in order that it should be possible to place its end sufficiently far into the nasal cavity without the remainder of the probe touching the nasal mucous membrane. As a result, there is in most cases not enough room for the end portion of the probe between the rhinostereometer and the nose.

This problem is solved by attaching the end of the probe on a positioning means, which is supported by a stand advantageously consisting of the rhinostereometer, and introducing, in a two-step operation, the end of the probe into the nose. In a first step, the end of the probe is brought to a position on or close to the optical axis of the rhinostereometer a certain distance into the nose by pivoting the positioning means about a pivot point located at a distance from the optical axis and, in a second step, the end of the probe is moved along the optical axis until it has come to occupy the position defined with the aid of the rhinostereometer, more specifically its plane of accurate focus, by moving the positioning means in parallel with the optical axis. Owing to the fact that the positioning means is supported by a stand, the problems associated with manual positioning of the probe, e.g. tremblings of the hand with ensuing inaccuracies, are avoided.

In order that the end of the probe should be able to enter the nose, the probe is suitably turned on the holder in the plane of the pivotal movement, while the positioning means is pivoted.

To many people, the introduction of an object into a body cavity is associated with feelings of discomfort. To enable the probe to be brought directly to the aimed-at position on or close to the nasal mucous membrane, thus minimising the time required for the introduction, a preliminary adjustment without the cooperation of the patient is advantageously performed. Owing to this preliminary adjustment, the end of the probe may then be directly brought to the right position.

It will be appreciated that the above technique for positioning a probe on the nasal mucous membrane may also be used for positioning a probe in other body cavities of a human being or an animal, for instance in the ear or the brain in connection with an operation. This technique may also serve to position a probe in other open cavities of an optional object. For instance, the probe might be a tube intended for the introduction of a substance into the cavity, an instrument for taking a sample of something in the cavity, or an optical instrument, such as an endoscope, for enlarging some part of the cavity.

One may furthermore consider using other optical techniques than rhinostereometry. What matters is that one is able to look into the open cavity in order to select a target surface and that the position of this surface in relation to a reference point, for instance the optical instrument used, can be defined with the aid of the technique employed. Moreover, the optical instrument should, as mentioned in the foregoing, be located outside the cavity.

BRIEF DESCRIPTION OF THE DRAWINGS

A few embodiments of the invention will now be described with reference to the accompanying drawings, in which.

DESCRIPTION OF PREFERRED EMBODIMENTS

Figure 1:
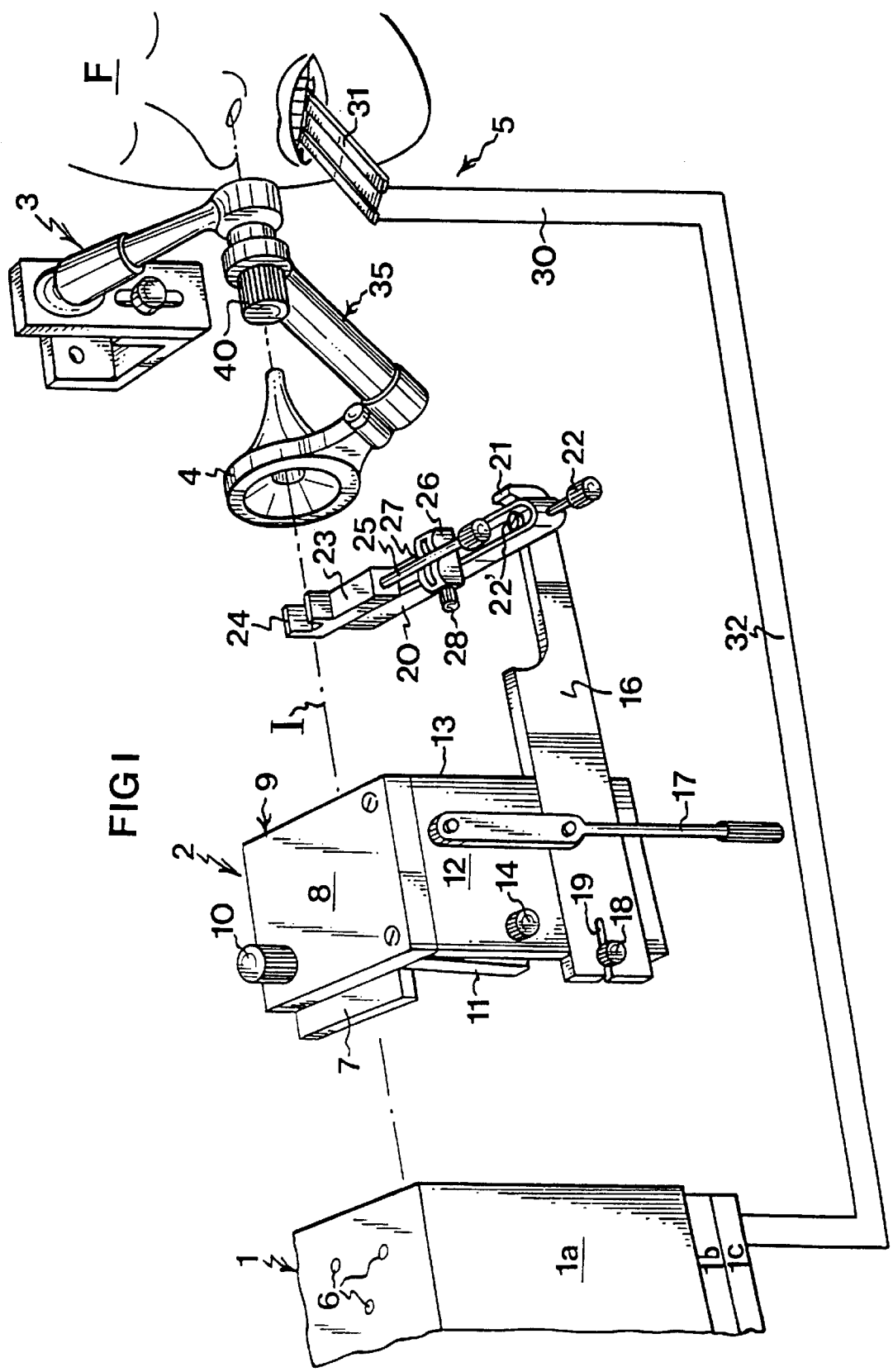
FIG. 1 is a schematic perspective view of an embodiment of the inventive system, the measurement being performed on a person.

For the sake of clarity, FIG. 1 shows the different components (separated along an optical axis I) of a system for positioning a probe on a given location on the nasal mucous membrane of a test subject F. The system according to the invention chiefly comprises a rhinostereometer 1, a positioning device 2, a holder 3 for a nose funnel 4, and a fixing device 5 for fixing the head of the test subject F in such a manner that the nasal mucous membrane occupies a fixed position in space.

The rhinostereometer 1, which can be purchased via AB Micromus, Box 10306, S-100 55 Stockholm, Sweden, comprises a surgical microscope, of which only the microscope head 1a is partly shown in FIG. 1 and which is so positioned on a micrometer table 1b as to be movable in three orthogonal directions, of which two are located in the horizontal plane. The micrometer table 1b is in turn arranged on a frame 1c. The microscope, which preferably is rotatable in the horizontal plane, comprises a lens and an eyepiece, which are chosen with a view to providing a shallow depth of field. The well-defined area that can be observed through the microscope is, in the positioning of the probe, used for defining the target surface of the probe. Conveniently, the microscope is so oriented that the well-defined area is almost perpendicular to one of the horizontal axes. The eyepiece is provided with a millimeter scale, which is substantially parallel to the other horizontal axis in the system.

The positioning device 2 is adapted to be attached directly on the rhinostereometer 1, more specifically on the upper side of the microscope head 1a, where three holes 6 are provided in order to receive three similarly-arranged pins (not shown) provided on the positioning device. Alternatively, the positioning device may be fixedly connected to the frame 1c of the micrometer table. It is further conceivable to attach the positioning device 2 on a separate stand. It goes without saying that the position of the positioning device in relation to the rhinostereometer has to be well-defined. In all cases, the positioning device is thus supported by a stand, either directly or via the rhinostereometer.

The positioning device comprises a first top plate 7, which is horizontally arranged and on whose underside the above-mentioned pins 6 are provided, and a second top plate 8, which is attached to the first top plate 7 by means of an articulation 9 at the edge of the first top plate 7 that, in the direction of the optical axis, is located opposite to the microscope head. A fine-adjustment screw 10 makes it possible to adjust the angle between the first and the second top plate 7, 8.

A first lateral plate 11 is attached to the one lateral edge of the second top plate 8 and extends at an angle of substantially 90° to the top-plate assembly 7, 8. A second lateral plate 12 is attached to the first lateral plate 11 with the aid of an articulation 13, which is placed at the edge of the first lateral plate 11 that, in the direction of the optical axis, is located opposite to the microscope head. A fine-adjustment screw 14 makes it possible to adjust the angle between the first and the second lateral plate 11, 12.

Instead of being fixedly connected to the second top plate 8, the first and the second lateral plate 11 and 12 may be movably connected thereto, so that their vertical position in relation to the second top plate 8 can be adjusted, for instance with the aid of an adjustment screw.

A first positioning means in the form of a sliding element 16 is slidably mounted in the second lateral plate 12 so as to be displaceable along a first axis, which is essentially parallel to the optical axis of the rhinostereometer. A lever 17 is attached to the second lateral plate 12 as well as to the sliding element 16, to enable the latter to be easily and expediently displaced with the aid of the lever 17. The end position of the sliding element 16 in the direction away from the microscope head is defined with the aid of an end position screw 18, which is displaceable in a groove 19 formed in the sliding element 16, and a stop element (not shown) provided on the second lateral plate.

A second positioning means in the form of an arm 20 is pivotally mounted on the end of the sliding element 16 that is located opposite to the end-position screw. The arm 20 can be pivoted about a second axis, which is perpendicular to the first axis, from a position in which it is essentially parallel to the sliding element to a position in which it is perpendicular thereto. The latter position is defined by a stop element 21, which is provided on the sliding element 16 and which prevents the arm 20 from being pivoted any further. The pivotal radius of the arm 20 is adjustable with the aid of an adjustment screw 22, which comes into abutment against a screw 22', which is screwed into the sliding element 16 and constitutes the pivot point of the arm 20. This pivot point may be displaced in the longitudinal direction of the arm in a slit and be locked with the aid of the adjustment screw 22. The pivot point is located at a distance from the optical axis.

Figure 2:
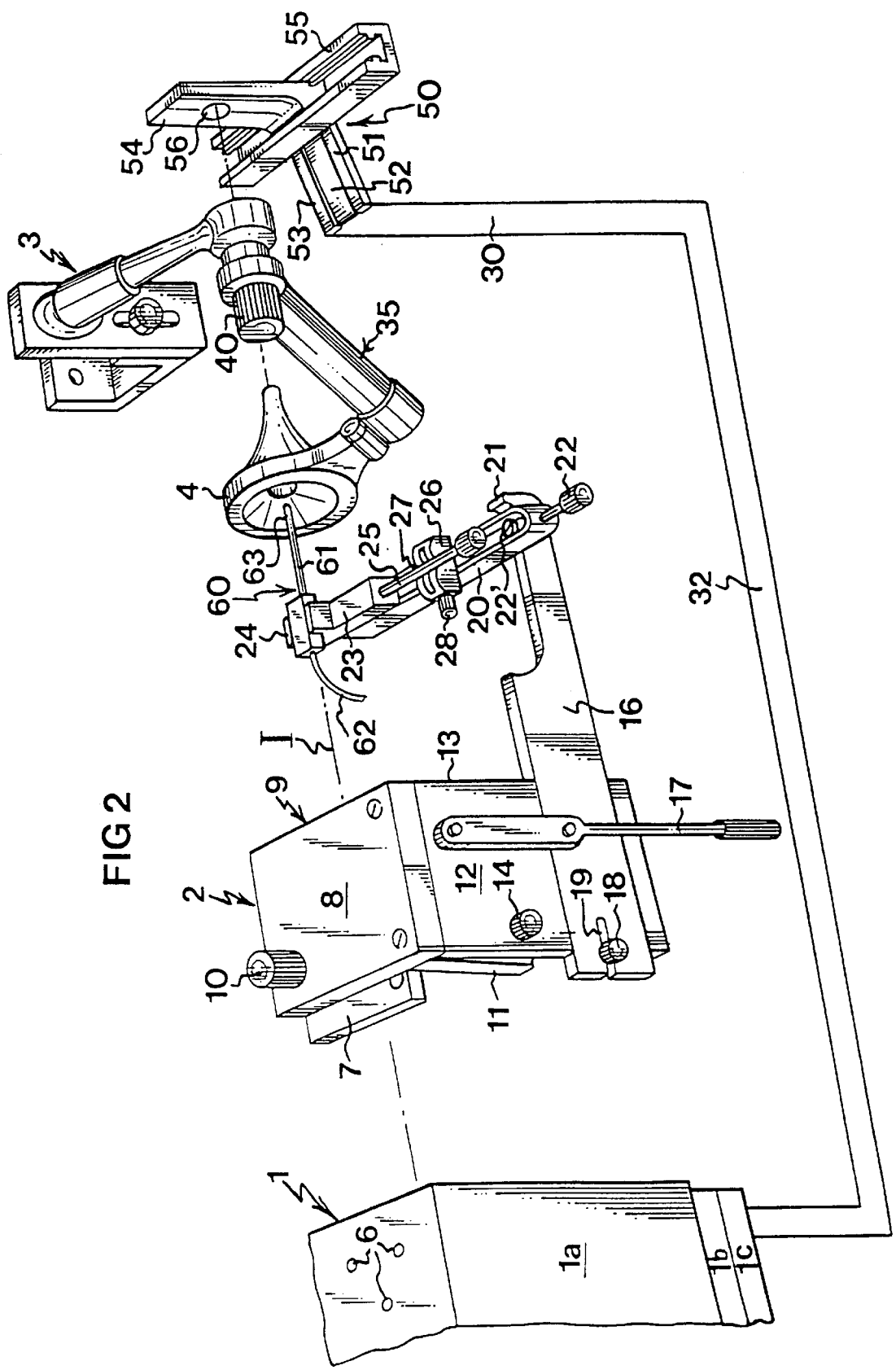
FIG. 2 is a schematic perspective view similar to that of FIG. 1, except for the fact that the test subject has been replaced with a dummy which will be used for the adjustment of the system.

A probe attachment 23 is so mounted on the end of the arm 20 that is located farthest away from the sliding element. 16 as to be turnable about an essentially vertical axis. The attachment 23 is provided with a recess 24 where a probe can be fixed by snap-in action, as illustrated in FIG. 2. The attachment 23 is further equipped with a lever 25, by means of which it can be easily and expediently turned in the pivotal plane of the arm 20.

On the arm 20, there is further provided an element 26 for fixing the attachment lever 25. This fixing element 26 extends transversely of the longitudinal direction of the arm 20 and has a recess 27, in which the attachment lever 25 can be fixed. The position of the fixing element in the transverse direction in relation to the arm 20 can be adjusted with the aid of an adjustment screw 28, a fine adjustment of the angular position of the attachment being obtainable.

The positioning device has an alignment axis I which is parallel to the sliding element 16. When the device is mounted on the rhinostereometer, the alignment axis I should essentially coincide with the optical axis of the rhinostereometer.

Further, the fixing device 5 comprises a stand 30, on which is fixedly mounted an acrylic splint 31 individually designed for each patient. With the aid of the acrylic splint 31, the test subject, or to be more specific the head of the test subject and, hence, his nasal mucous membrane, can be fixed in a given position in space or a coordinate system.

Preferably, the fixing device 5 is fixedly connected to the frame 1c of the rhinostereometer by means of a connecting element 32, so that the patient may repeatedly be placed in one and the same position in relation to the frame 1c of the rhinostereometer.

The holder 3, which preferably is attached on the fixing device 5, comprises an articulated arm 35 on which is mounted the nose funnel 4, which may be a conventional ear speculum or a nasal speculum. The articulated arm 35 may either be movable in a versatile manner, such that the articulation elements are freely movable in relation to each other, or be fixed with the aid of an adjustment screw 40, such that the articulation elements are fixed in relation to each other.

The system illustrated in FIG. 1 operates as follows. When a probe is to be positioned on or adjacent to the nasal mucous membrane of a patient, the head of the patient F is first fixed in space or in a coordinate system with the aid of the fixing device 5 by having the patient bite into the acrylic splint 31 of individual design. In order to widen the nostril slightly and keep aside hair and mucus, the nose funnel 4 is then introduced into the nostril into which the probe is later to be inserted.

In the next step, the person conducting the examination looks through the rhinostereometer and chooses a target surface on the nasal mucous membrane by moving and pivoting the rhinostereometer so that the target surface comes to be located in its plane of accurate focus. When this is the case, the position of the nose funnel 4 is locked with the aid of the adjustment screw 40, as is the position of the rhinostereometer on the micrometer table 1b. In addition, one notes the position of the target surface on the scale in the eyepiece. Preferably, the rhinostereometer is so directed that the target surface is located at the centre of the millimeter scale, i.e. on the optical axis. However, it may, in some applications, be necessary or suitable to place the target surface at a small distance from the optical axis.

At this stage, the optical axis has been fixed, and the position of the target surface has been defined in relation to the rhinostereometer or in a coordinate system where the rhinostereometer serves as the origin of coordinates. The patient may then let go of the acrylic splint 31 and remove his nose from the nose funnel 4. The acrylic splint is then removed from the fixing device and replaced with a target-surface dummy 50 (shown in FIG. 2), which comprises a T-shaped element 51 that is formed with a groove 52 in the body 53 of the T and an auxiliary target surface 54 that is provided with a point of aim 56 and extends perpendicular to the plane of the T-shaped element 51 and is movable along the crossbar 55 of the T. The position of the auxiliary target surface 54 on the crossbar 55 of the T is so adjusted as to be located on the optical axis I of the rhinostereometer, and the attachment point for the target-surface dummy in the groove 52 is so adjusted that the auxiliary target surface 54 is located in the plane of accurate focus of the rhinostereometer and the point of aim 56 is located at the centre of the scale of the rhinostereometer. When this adjustment has been made, the auxiliary target surface thus occupies the same position in space as was previously occupied by the target surface on the nasal mucous membrane when the patient was fixed with the aid of the acrylic splint 31. However, the auxiliary target surface is by no means necessary, and the adjustment described in the following may also be performed by looking through the rhinostereometer to observe when the end of the probe has reached the correct position.

In the next step, a probe 60 is, as illustrated in FIG. 2, attached to the probe attachment 23 by snap-in action. When this happens, the arm is pivoted to a position in which it is almost parallel to the sliding element 16 and the pivot point 22' is adjusted to a position a certain distance in on the arm 20, such that the pivotal radius thereof is not maximal. The probe 60 comprises a rectilinear and rigid end portion 61, which is connected to a hose 62. The outermost end 63 of the end portion 61 should be slightly angled to enable it to be applied against an inclined surface. When the probe 60 has been attached by snap-in action, the arm 20 is pivoted on the sliding element 16. During this pivotal movement, the attachment lever 25 is movable, enabling the attachment 23 to be turned on the arm 20. During this pivotal movement, the pivotal radius of the arm 20 further increases until the arm comes into abutment against the stop element 21 on the sliding element 16. In this position, the end of the probe is located a certain distance into the nose funnel 4. Then, the attachment lever 25 is fixed on the fixing element 26. The position of the attachment 23 perpendicular to the sliding element is adjusted with the aid of the adjustment screw 22 on the arm 20, such that the probe end 63 is located essentially on the optical axis, and the angular position of the attachment 23 is finely adjusted with the aid of the adjustment screw 28 on the fixing element 26, such that the probe end 63 is located in the recorded place on the scale of the eyepiece and the remainder of the end portion of the probe is located essentially in parallel with the optical axis.

The position of the probe end in relation to the optical axis having been thus determined, the sliding element 16 is, with the aid of the lever 17, moved in the direction of the auxiliary target surface 54. When approaching the auxiliary target surface 54, the probe end 63 can be seen through the rhinostereometer. If need be, one may then perform a fine adjustment of the position of the probe end in relation to the optical axis with the aid of the adjustment screws 22 and 28, whereupon the probe end 63 is applied against the auxiliary target surface 54 on the point of aim 56 with the aid of the lever 17. The position of the sliding element 16 when the probe end occupies this position is registered by moving the end-position screw 18 in the groove 19 so that it comes to be applied against the stop (not shown) and is fixed. The positioning device has now been pre-set to enable the probe end 63 to be brought directly to the correct position on the nasal mucous membrane of the patient.

The sliding element 16 is then withdrawn with the aid of the lever 17, the arm 20 is pivoted away, and the attachment lever 25 is unfixed to enable the probe 60 to be moved out of the nose funnel 4 and away from the optical axis I. The holder 3 for the nose funnel is rendered movable in a versatile manner, and the target-surface dummy 50 is replaced with the patient's acrylic splint 31, whereupon the patient anew has to bite into the splint so that the target surface on the nasal mucous membrane is once more fixed in the position it had when the rhinostereometer was adjusted. Then, the nasal funnel 4 is once more introduced into the patient's nostril and so positioned that the optical axis is located at the centre of the nose funnel.

The probe end 63 may now easily and expediently be placed in the correct position on the nasal mucous membrane by pivoting the arm 20 until it comes to be applied against the stop element 21 on the sliding element 16, attaching the attachment lever 25 on the stop element 26, and bringing the sliding element 16 with the aid of the level 17 to the end position defined by the end-position screw 18.

If the degree of swelling of the nasal mucous membrane alters during the measurement in the nose, the position of the probe end 63 perpendicular to the optical axis can be adjusted with the aid of the fine-adjustment screw 14 on the lateral-plate assembly 11, 12.

When the positioning device is put to use, the second top plate 9 is preferably angled somewhat in relation to the first top plate 8, so that the longitudinal axis of the sliding element 16 is angled somewhat in the vertical plane in relation to the optical longitudinal axis, such that it is only the end 63 of the probe that is located directly on the optical axis, the remainder of the rigid end portion of the probe being slightly angled in relation to the optical axis in the vertical plane. In this manner, the probe end will not be hidden by the remainder of the probe.

As an alternative to the mode of operation described above, the pre-setting can be performed without the patient taking part at all. One then begins by adjusting the rhinostereometer in relation to the auxiliary target surface of the target-surface dummy, so that this surface comes to be located in the plane of accurate focus of the rhinostereometer. (The fixing device has been moved aside and is not used). Then, the probe 60 is fixed on the attachment 23 on the arm 20, which may be pivoted to the position perpendicular to the sliding element 16, since the nose funnel 4 is not in the way. The attachment lever 25 is fixed on the fixing device, and the arm 20 is moved in parallel with the optical axis with the aid of the sliding element 16, so that the end 63 of the probe 60 come3 to be applied against the auxiliary target surface 54. When the probe end is close to the auxiliary target surface 54, it can be seen through the rhinostereometer, and its position can be finely adjusted with the aid of the adjustment screws 28 and 22. When the probe end 63 occupies the aimed-at position, the position of the sliding element 16 is registered with the aid of the screw 18. The pre-setting operation has now been completed. When the probe end is to be positioned on the patient, the target-surface dummy 50 is replaced with an acrylic splint which the patient bites into. The nasal funnel 4 is introduced into the patient's nostril and is fixed. The rhinostereometer is so adjusted that the target surface on the patient is visible in the plane of accurate focus. Unless the optics of the rhinostereometer have been adjusted, the target surface is now located in the same position in relation to the rhinostereometer as was previously occupied by the auxiliary target surface. Since the positioning device is fixedly connected to the rhinostereometer, the probe end 63 may now be positioned on the target surface by pivoting the arm 20, fixing the attachment lever 25 on the fixing device 27, and moving the sliding element 16 to the position defined by the adjustment screw 18.

It goes without saying that the above embodiments and modes of operation are but examples, which can be modified in many ways within the scope of the appended claims. For instance, the positioning device need not be pre-set, the probe end being then positioned directly on the nasal mucous membrane by means of the positioning device.

What is claimed is:

1. A method for positioning an end of a probe on a target surface inside an open cavity in a test object, comprising the steps of fixing the test object in a given position; adjusting an optical instrument in such a manner that the target surface is located essentially on its optical axis and the position of the target surface in the longitudinal direction of the optical axis is defined; attaching the probe on a pivotable arm, which is supported by a stand; causing the pivotable arm to perform a pivotal movement about a pivot point located at a distance from the optical axis, such that the end of the probe is positioned essentially on the optical axis a certain distance into the open cavity; and thereafter moving the pivotable arm in parallel with the optical axis, such that the end of the probe reaches the target-surface position defined with the aid of the optical instrument.

2. A method as claimed in claim 1, comprising the further steps of turning the probe on the pivotable arm in the plane of the pivotal movement while causing the pivotable arm to perform the pivotal movement.

3. A method as claimed in claim 2, comprising the further steps of removing the test object from the given position after the optical instrument has been adjusted; and, after the end of the probe has been moved to the target-surface position defined by the optical instrument, recording the position of the pivotable arm, moving the pivotable arm such that the end of the probe will no longer be located in the target-surface position defined by the optical instrument, again fixing the test object in the given position, and moving the end of the probe to the target-surface position defined by the optical instrument by operating the pivotable arm to the recorded position.

4. A method as claimed in claim 2, comprising the further steps of, before the test object is fixed in a given position, so adjusting the optical instrument that an auxiliary target surface occupies a defined position in the longitudinal direction on the optical axis of the instrument, carrying out the attachment of the probe on the pivotable arm, operating the pivotable arm in such a manner that the end of the probe is located on the auxiliary target surface, recording the position of the pivotable arm, moving the pivotable arm so that the end of the probe no longer is located on the auxiliary target surface, and removing the auxiliary target surface, the adjustment of the optical instrument after the test object has been fixed in a given position being carried out in such a manner that the target surface is placed in the same position in relation to the optical instrument as was previously occupied by the auxiliary target surface, and the pivotal movement of the pivotable arm and the displacement of the pivotable arm in parallel with the optical axis being performed with the aid of the recorded position of the pivotable arm.

5. A method as claimed in claim 1, comprising the further steps of removing the test object from the given position after the optical instrument has been adjusted; and, after the end of the probe has been moved to the target-surface position defined by the optical instrument, recording the position of the pivotable arm, moving the pivotable arm such that the end of the probe will no longer be located in the target-surface position defined by the optical instrument, again fixing the test object in the given position, and moving the end of the probe to the target-surface position defined by the optical instrument by operating the pivotable arm to the recorded position.

6. A method as claimed in claim 5, comprising the further steps of placing, after the test object has been removed from the given position, an auxiliary target surface on the optical axis and displacing this target surface until it reaches the target-surface position defined by the optical instrument.

7. A method as claimed in claim 1, comprising the further steps of, before the test object is fixed in a given position, so adjusting the optical instrument that an auxiliary target surface occupies a defined position in the longitudinal direction on the optical axis of the instrument, carrying out the attachment of the probe on the pivotable arm, operating the pivotable arm in such a manner that the end of the probe is located on the auxiliary target surface, recording the position of the pivotable arm, moving the pivotable arm so that the end of the probe no longer is located on the auxiliary target surface, and removing the auxiliary target surface, the adjustment of the optical instrument after the test object has been fixed in a given position being carried out in such a manner that the target surface is placed in the same position in relation to the optical instrument as was previously occupied by the auxiliary target surface, and the pivotal movement of the pivotable arm and the displacement of the pivotable arm in parallel with the optical axis being performed with the aid of the recorded position of the pivotable arm.

8. A device for positioning an end of a probe on a target surface inside an open cavity in a test object, the device being intended for use along with an optical instrument, the device being adapted to define a position of the target surface, the device being adapted to be supported by a stand and having an alignment axis which essentially coincides with the optical axis of the optical instrument when the device is in use, the device comprising:

a sliding element which is displaceable along a first axis that is parallel to the alignment axis of the device, and a pivotable arm which is connected to the sliding element and on which is provided an attachment for the probe, the pivotable arm being pivotable in relation to the sliding element about a second axis which is perpendicular to the first axis, such that the attachment can be brought to a position essentially on the alignment axis, wherein there are provided means for establishing the position of the attachment on the pivotable arm.

9. A device as claimed in claim 8, wherein the device is adapted to be supported by the optical instrument.

10. A system for positioning an end of a probe on a target surface inside an open cavity in a test object, wherein there are provided a device for fixing the test object in a given position, an optical instrument for defining the position of the target surface, and a device for positioning an end of the probe on the target surface inside the open cavity in the test object, the device being intended for use along with the optical instrument, the device being adapted to define a position of the target surface, the device being adapted to be supported by a stand and having an alignment axis which essentially coincides with the optical axis of the optical instrument when the device is in use, the device comprising a sliding element displaceable along a first axis parallel to the alignment axis of the device, and a pivotable arm connected to the sliding element and on which is provided an attachment for the probe, the pivotable arm being pivotably attached to the sliding element by a member having a second axis which is perpendicular to the first axis, such that the pivotable arm is pivotable only in a single plane perpendicular to the second axis and the attachment can be brought to a position essentially on the alignment axis, said device being attached to the optical instrument in such a manner that its alignment axis coincides with the optical axis of the optical instrument.

11. A system as claimed in claim 10, wherein the optical instrument comprises a microscope, which is mounted on a frame in such a manner as to be displaced in three orthogonal directions, the position of the target surface being defined by displacing the microscope so that the target surface is located in the place of accurate focus of the microscope.

12. A system as claimed in claim 11, wherein there is provided an auxiliary target surface which is attachable on the fixing device.

13. A system as claimed in claim 10, wherein there is provided an auxiliary target surface, which is attachable on the fixing device.

* * * * *